(12) United States Patent
Sauer

(10) Patent No.: US 11,612,736 B2
(45) Date of Patent: Mar. 28, 2023

(54) MINIMALLY INVASIVE VAD INSTALLATION SYSTEM AND METHOD

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 162 days.

(21) Appl. No.: 16/846,087

(22) Filed: Apr. 10, 2020

(65) Prior Publication Data
US 2020/0324032 A1 Oct. 15, 2020

Related U.S. Application Data

(60) Provisional application No. 62/831,860, filed on Apr. 10, 2019.

(51) Int. Cl.
*A61M 1/10* (2006.01)
*A61M 60/148* (2021.01)
*A61M 60/892* (2021.01)
*A61M 60/232* (2021.01)
*A61M 60/178* (2021.01)
*A61M 60/865* (2021.01)
*A61M 60/863* (2021.01)

(52) U.S. Cl.
CPC ........ *A61M 60/148* (2021.01); *A61M 60/178* (2021.01); *A61M 60/232* (2021.01); *A61M 60/863* (2021.01); *A61M 60/865* (2021.01); *A61M 60/892* (2021.01)

(58) Field of Classification Search
CPC ............ A61M 1/10; A61M 1/12; A61B 17/11
See application file for complete search history.

(56) References Cited

U.S. PATENT DOCUMENTS

2013/0116668 A1* 5/2013 Shelton, IV ......... A61B 17/068 606/1

* cited by examiner

*Primary Examiner* — Matthew W Schall
(74) *Attorney, Agent, or Firm* — Michael E. Coyne; Christopher B. Miller

(57) ABSTRACT

A minimally invasive VAD installation system is disclosed. The installation system has a curved hook having another hook at its distal end. The installation system also has a valve insertion tool having a gimbaled set of clamp jaws configured for releasably holding the inflow tube of a VAD pump. The installation system further has a pushing tool having a distal opening configured to pass over a tube.

13 Claims, 20 Drawing Sheets

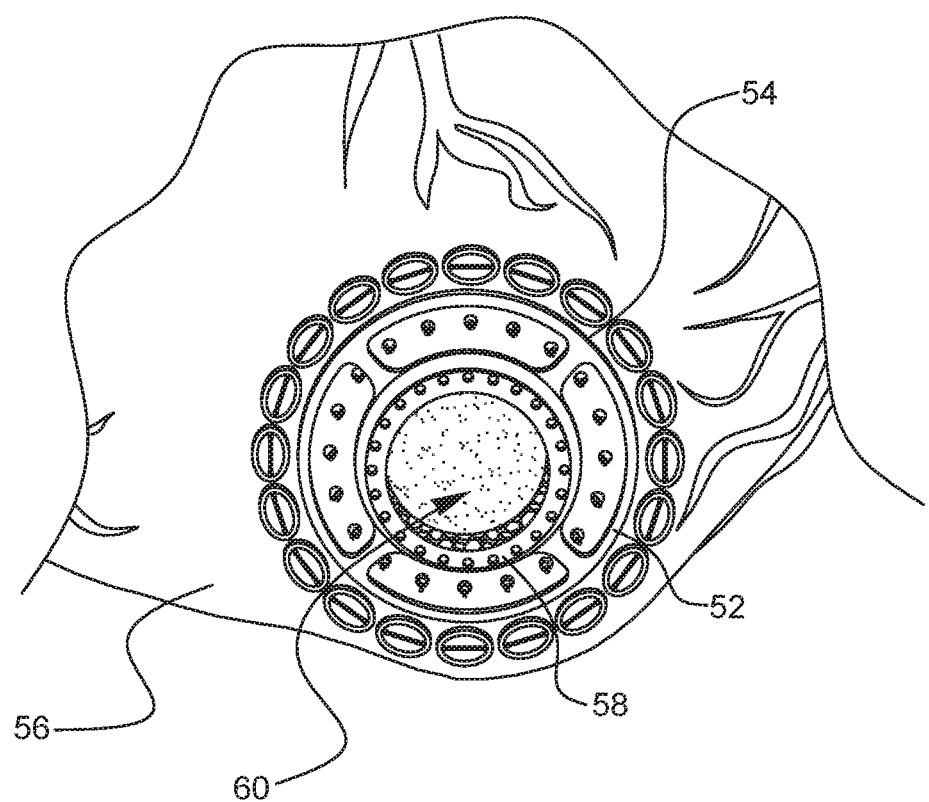
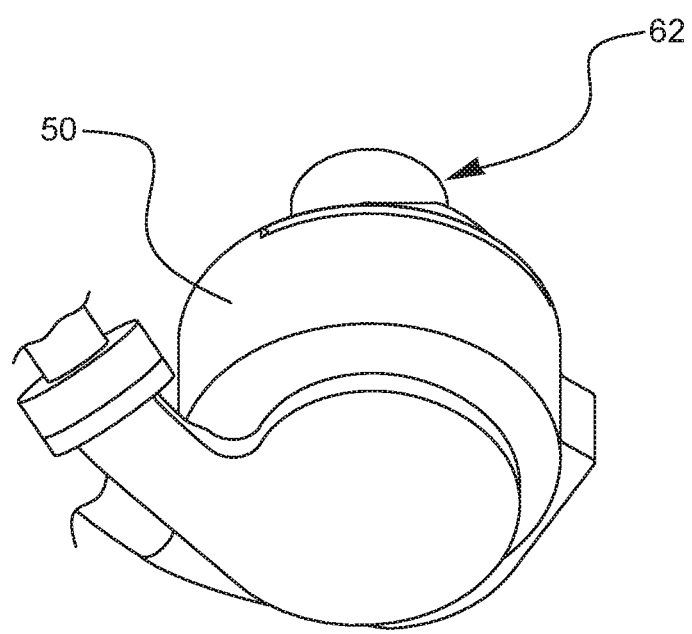
FIG. 1

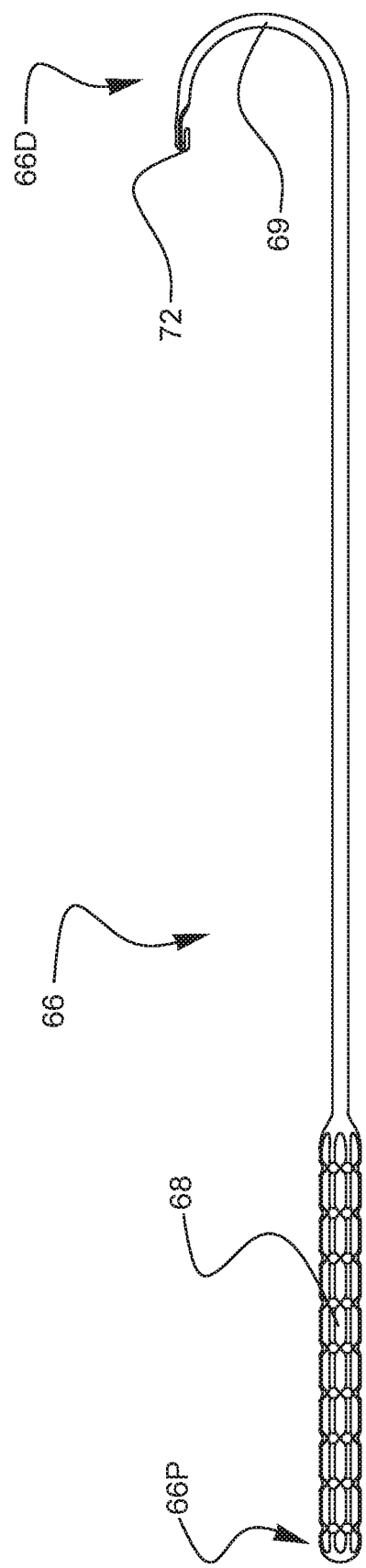
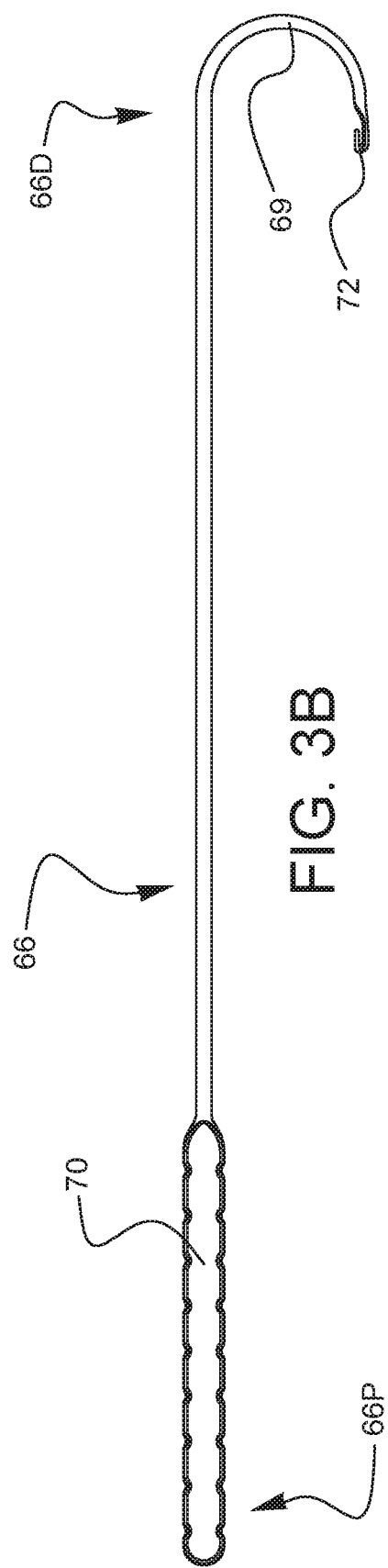

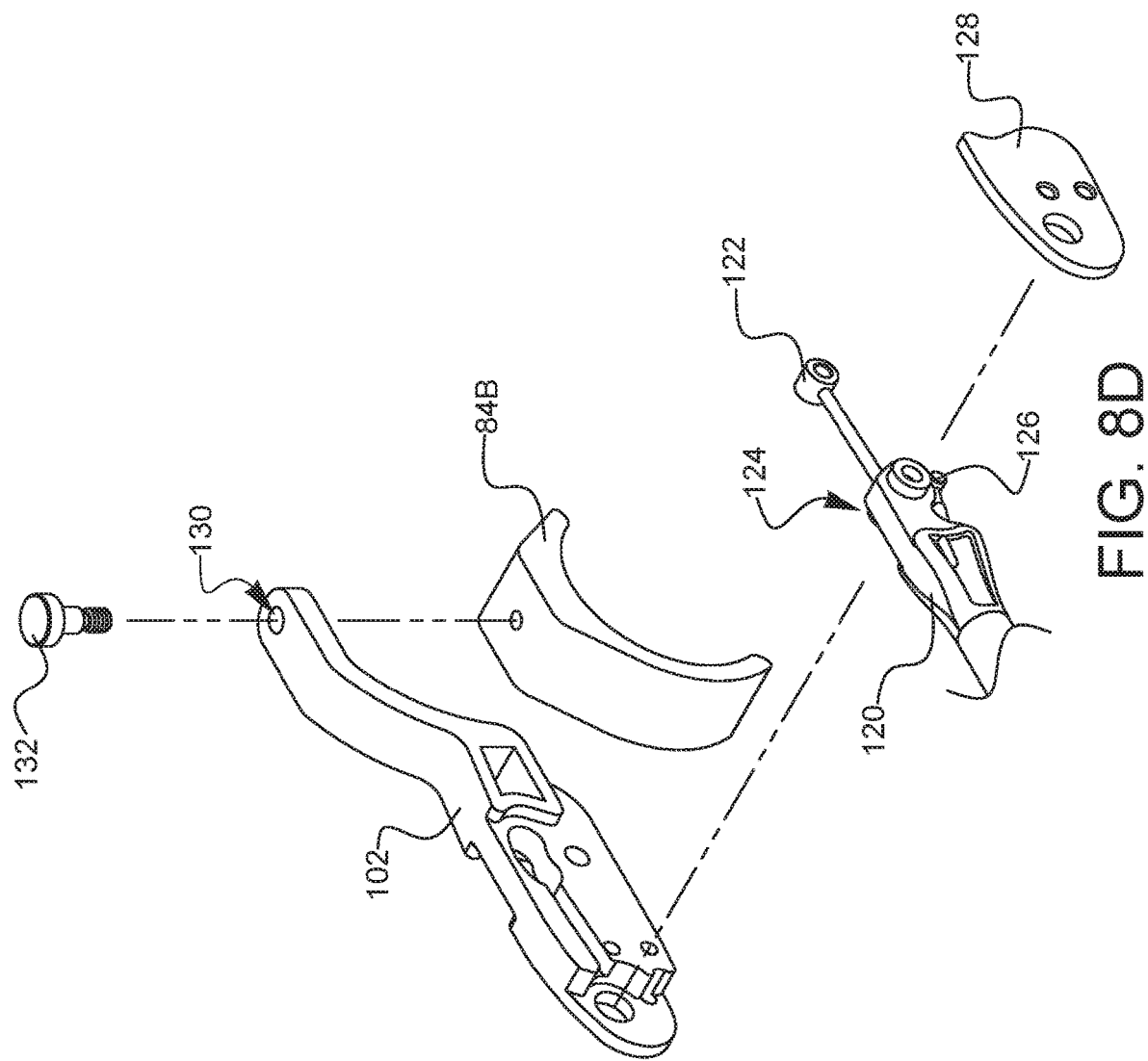

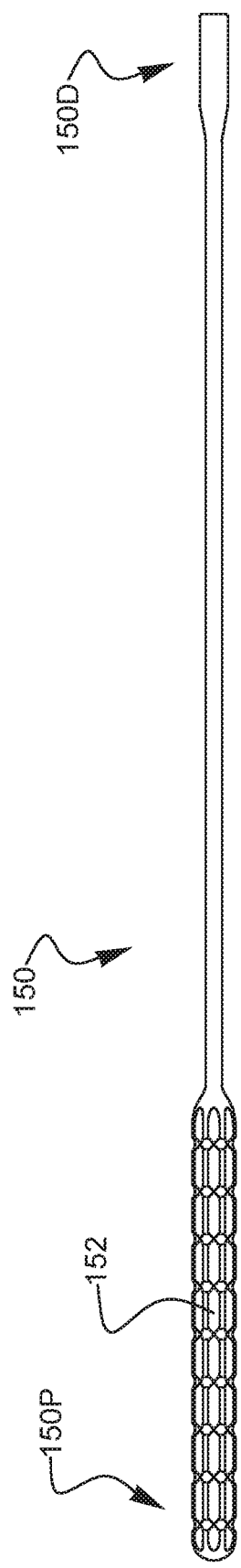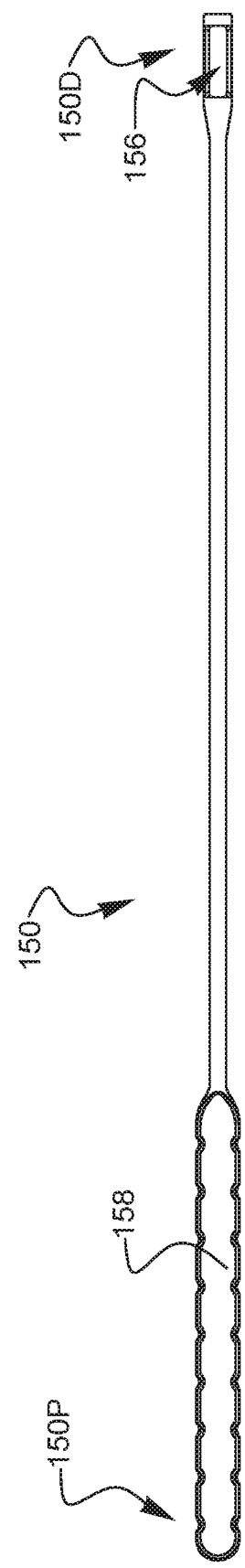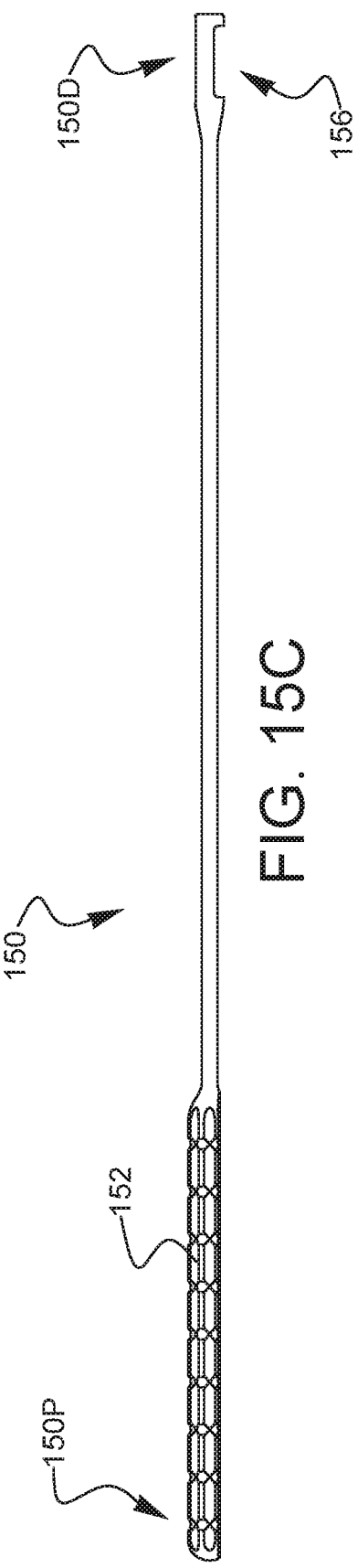

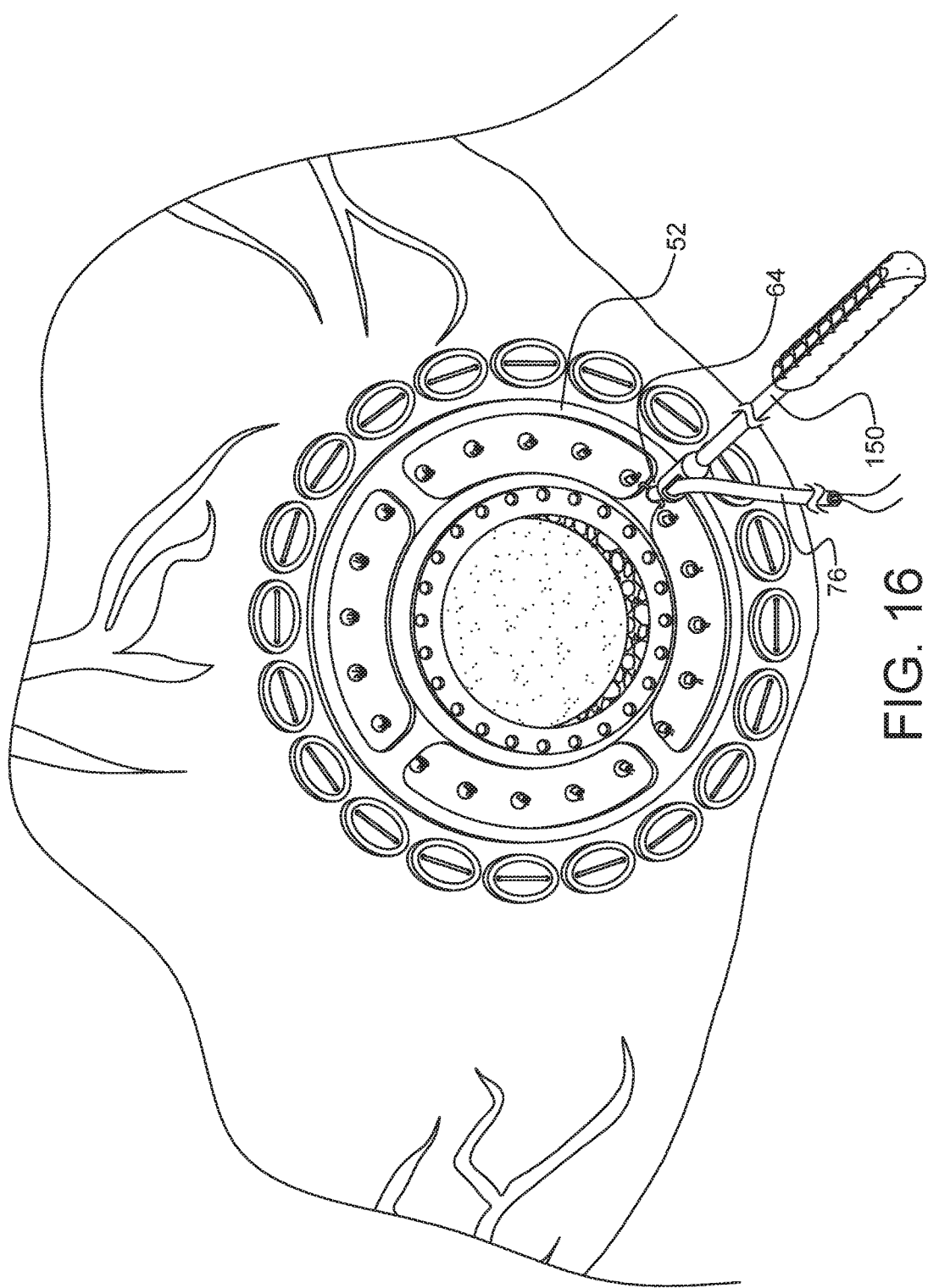

MINIMALLY INVASIVE VAD INSTALLATION SYSTEM AND METHOD

RELATED APPLICATIONS

This application claims priority to U.S. Provisional Patent Application No. 62/831,860 filed Apr. 10, 2019 and entitled, "MINIMALLY INVASIVE VAD INSTALLATION SYSTEM AND METHOD". The 62/831,860 application is hereby incorporated by reference in its entirety.

FIELD

The claimed invention relates to surgical devices, and more specifically to surgical devices to assist with the minimally invasive installation of a ventricular assist device (VAD) such as a left ventricular assist device (LVAD).

BACKGROUND

Patients suffering from heart disease are often dealing with a progressively worsening situation when it comes to the viability of their heart. Due to underlying congenital and/or physical factors, the heart is continually pushed more and more until the point where the heart becomes unable to push hard enough to circulate blood effectively throughout the patient's body. At his point, if a patient does not receive a heart transplant, the patient will often die of congestive heart failure or one of a number of complicating scenarios. Unfortunately, the number of patients in need of a heart transplant far exceeds the number of donor hearts which are available.

Fortunately, a technology called a ventricular assist device (VAD) has been developed to help provide a "bridge to transplant". A VAD is a pump which is coupled between a patient's ventricle and the circulatory structure which the ventricle was meant to supply with blood. In the case of the right ventricle, an inflow side of the VAD could be inserted through the heart wall into the right ventricle, while the outflow side of the VAD could be reconnected into the pulmonary artery which feeds blood to the lungs. In the case of the left ventricle, an inflow side of the VAD could be inserted through the heart wall into the left ventricle, while the outflow side of the VAD could be reconnected into the aorta which feeds blood to the rest of the patient's body. The left ventricle often is most in need of assistance for such patients, so for convenience, the remainder of this specification will discuss the inventive concepts herein with regard to left ventricular assist devices (LVADs). However, it should be understood that other types of VADs would be applicable, too.

The traditional manner of installing an LVAD is via a full sternotomy. The full access provided to the patient's chest with a sternotomy makes it simpler for the LVAD to be installed, since typically, one surgeon is attaching the pump to the ventricle while another surgeon is creating an anastomosis for the outflow into the aorta. Unfortunately, there are at least two major downsides to installing an LVAD through a full sternotomy. First, the patient will experience significant post-operative pain and a long recovery time with the full sternotomy. Second, since the LVAD is merely a bridge to transplant, if a transplant heart later becomes available for the patient, the adhesions and scar tissue under the healed sternotomy can be very difficult to cut through for the heart transplant. Therefore, it would be desirable to have a minimally invasive LVAD installation system and method which does not require a sternotomy, thereby improving patient outcomes.

SUMMARY

A minimally invasive VAD installation system is disclosed. The installation system has a curved hook having another hook at its distal end. The installation system also has a valve insertion tool having a gimbaled set of clamp jaws configured for releasably holding the inflow tube of a VAD pump. The installation system further has a pushing tool having a distal opening configured to pass over a tube.

BRIEF DESCRIPTION OF THE DRAWINGS

FIG. 1 illustrates an example ventricular assist device positioned for installation onto a flange which has been surgically attached to the apex of a heart.

FIGS. 3A and 3B are front and rear elevational views, respectively of a curved hook which can be manipulated through a thoracotomy and pivoted under each of the crossbars of a flange in turn to snare a suture and pull it under the crossbar and out of the thoracotomy.

FIGS. 8A-8E are exploded perspective views of portions of the insertion tool of FIGS. 6 and 7 which illustrate their assembly.

FIGS. 15A, 15B, and 15C are top, bottom, and side elevational views, respectively of the pushing tool from FIG. 14.

FIG. 16 illustrates an example where the pushing tool has been placed over such a tube coupled to a flange crossbar.

Figure 2:
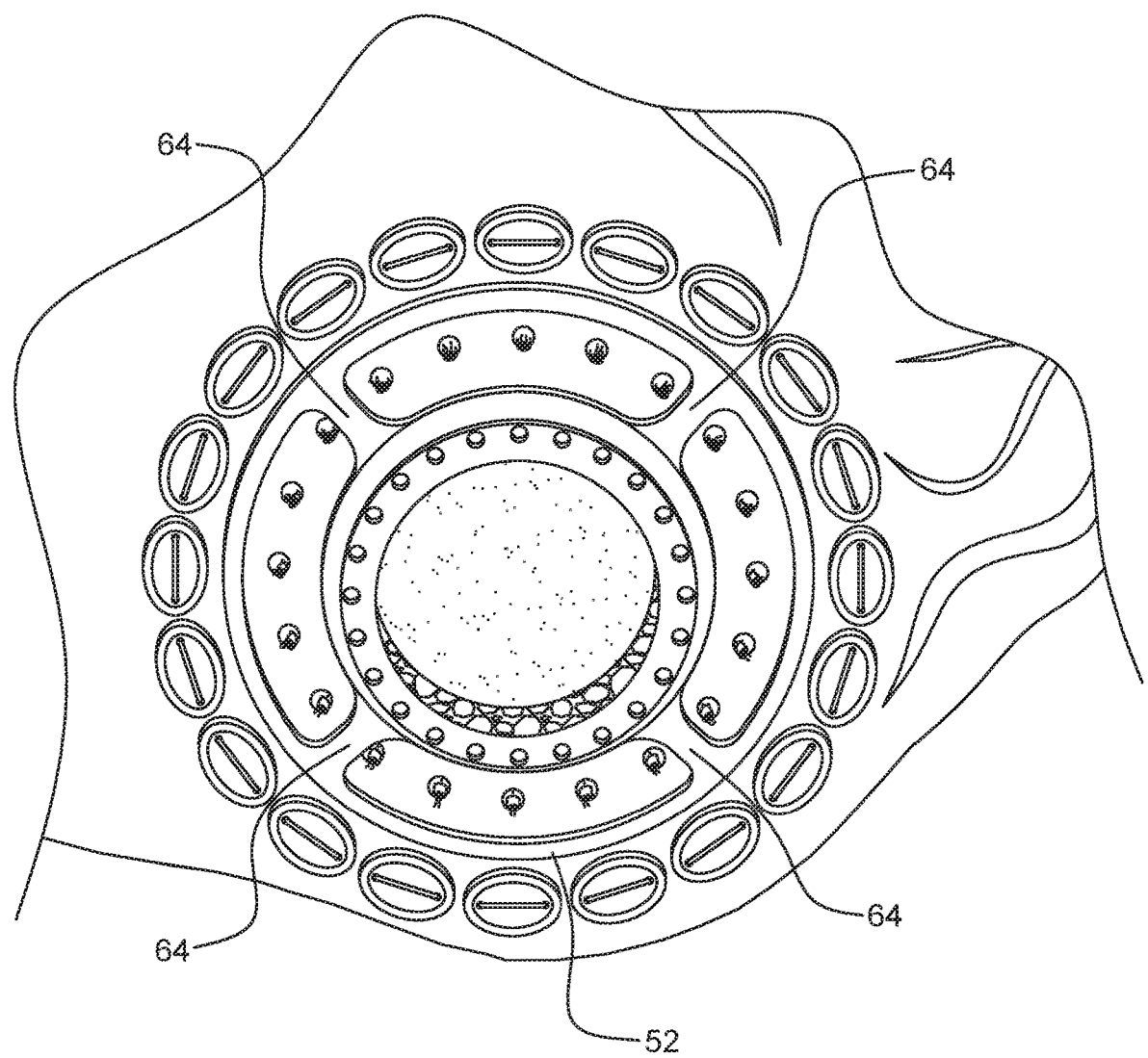
FIG. 2 is an enlarged view of the flange from FIG. 1

It will be appreciated that for purposes of clarity and where deemed appropriate, reference numerals have been repeated in the figures to indicate corresponding features, and that the various elements in the drawings have not necessarily been drawn to scale in order to better show the features

DETAILED DESCRIPTION

For convenience, this specification will discuss VAD installation within the context of use with a HeartMate III (HMIII) LVAD pump 50, such as the one illustrated in FIG. 1. It should be understood that the HMIII LVAD is just one example of a VAD which could be used with the embodiments of a minimally invasive VAD installation system that are described herein. A flange 52 having a sewing cuff 54 is supplied by the manufacturer. The sewing cuff 54 is sutured to the apex of the heart 56 along a circle 58 marked on the cuff in black. The opening 60 at the center of the flange is cored to provide access into the left ventricle. An HMIII pump 50 is shown ready to be inserted into the opening 60 in the flange 52. When this is attempted to be done through a small thoracotomy, however, rather than with a full sternotomy, it is difficult to work the pump 50 into the small thoracotomy access opening and further difficult to fit the pump inflow tube 62 into the flange opening 60 because this is done while the heart 56 is beating.

FIG. 2 is an enlarged view of the flange 52 from FIG. 1. In this example, the flange 52 has four crossbars 64 oriented radially every 90 degrees. The embodiments of VAD installation system and method disclosed herein are useful in helping to install the VAD onto the flange. Embodiments of the VAD installation system may comprise one or more of a curved hook, a valve insertion tool, and/or a pushing tool as disclosed in embodiments below.

FIGS. 3A and 3B are front and rear elevational views, respectively of a curved hook 66 which can be manipulated through a thoracotomy and pivoted under each of the crossbars in turn to snare a suture and pull it under the crossbar and out of the thoracotomy. The curved hook 66 has a proximal end 66P and a distal end 66D. The proximal end 66P has a textured grip 68 to assist with holding the curved hook 66. The curved hook 66 has a main hook 69. In this embodiment, the proximal end 66P also has an orientation feature 70, which can assist a user of the curved hook 66 with maintaining awareness of where the main hook 69 is pointing. This is especially useful when the main hook 69 portion of the curved hook 66 is inside a patient and can't be directly visualized. The curved hook 66 also has an additional hook 72 at the end of the main hook 69.

Figure 4A:
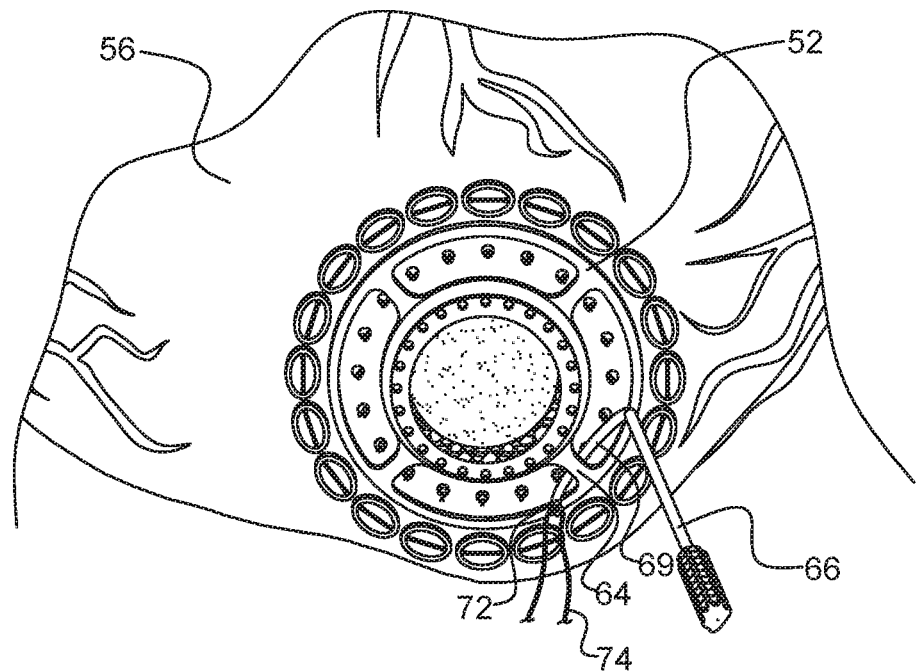
FIGS. 4A and 4B illustrate the process of using the curved hook to pull a suture under one of the flange crossbars while the flange is mounted to the heart.
Figure 4B:
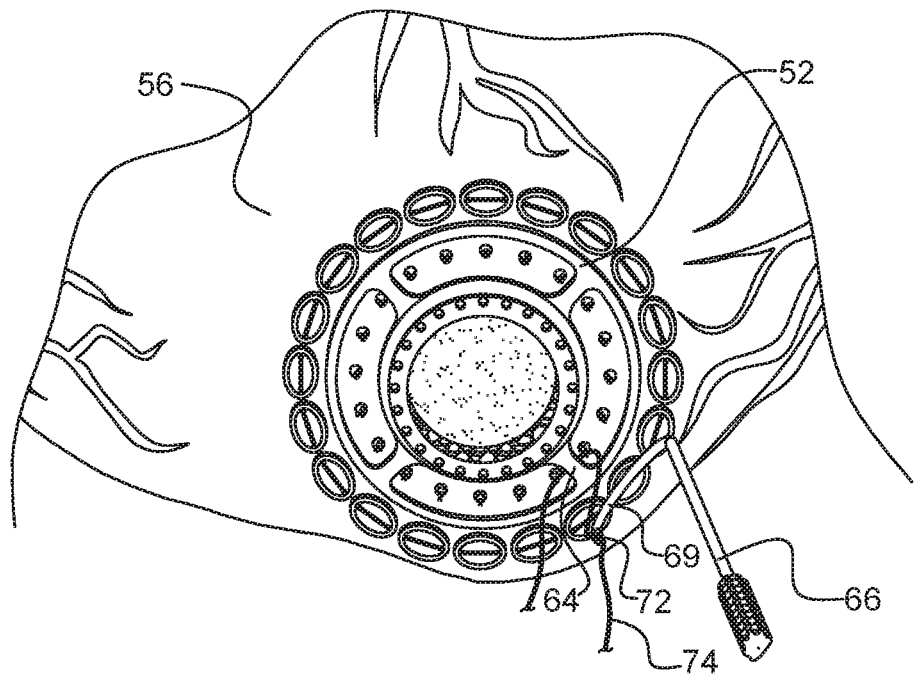

FIGS. 4A and 4B illustrate the process of using the curved hook 66 to pull a suture 74 under one of the flange crossbars 64 while the flange is 52 mounted to the heart 56. As shown in FIG. 4A, the main hook 69 is first hooked under the crossbar 64, while the additional hook 72 is manipulated to hook onto the suture 74. As shown in FIG. 4B, while curved hook 66 is manipulated so that the main hook 69 is pulled out from under the crossbar 64 while the additional hook 72 continues to hook the suture 74. In this way, a suture 74 may be placed under each crossbar 64 of the flange 52.

Figure 5:
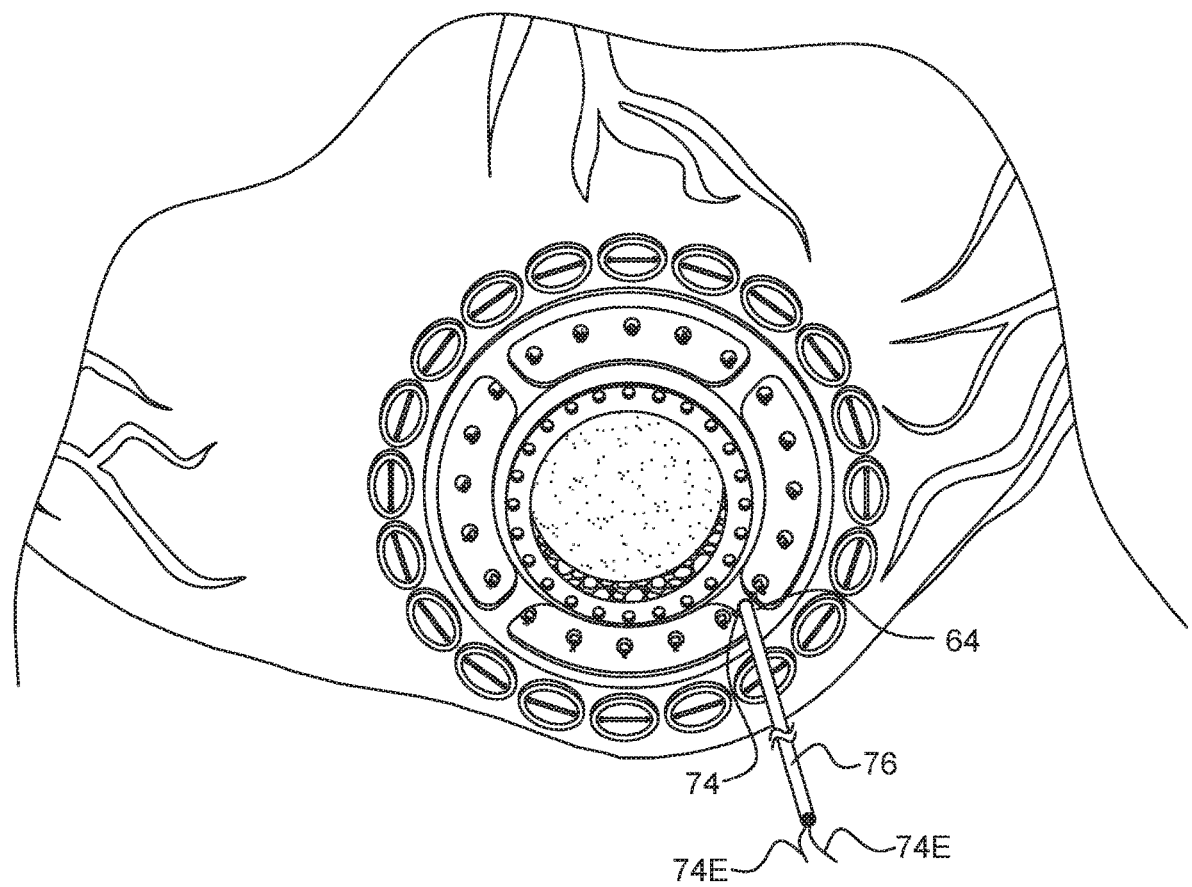
FIG. 5 illustrates one embodiment of a tube through which the ends of a flange-surrounding suture have been passed.

Once a suture 74 has been hooked behind a cross bar 64, the ends 74E of the suture 74 may be brought out of the patient, where they can be snared through a tube 76 such as the MINI-RUMEL™ Device from LSI Solutions, Inc., of Victor, N.Y. (www.lsisolutions.com). The suture ends 74E exiting the tube 76 can be clamped or otherwise crimped with a mechanical fastener or held to effectively couple the tube 76 to the crossbar 64. An example of such a tube 76 is shown in FIG. 5.

Since the surgeon is working through a mini thoracotomy, the tubes can be anchored to the outside of the patient's chest, for example, with a device such as the RAM® Ring provided by LSI Solutions, Inc. of Victor, N.Y. (www.lsisolutions.com). The coupled and secured tubes can act as a tether to help stabilize the flange while the heart is beating.

Figure 6:
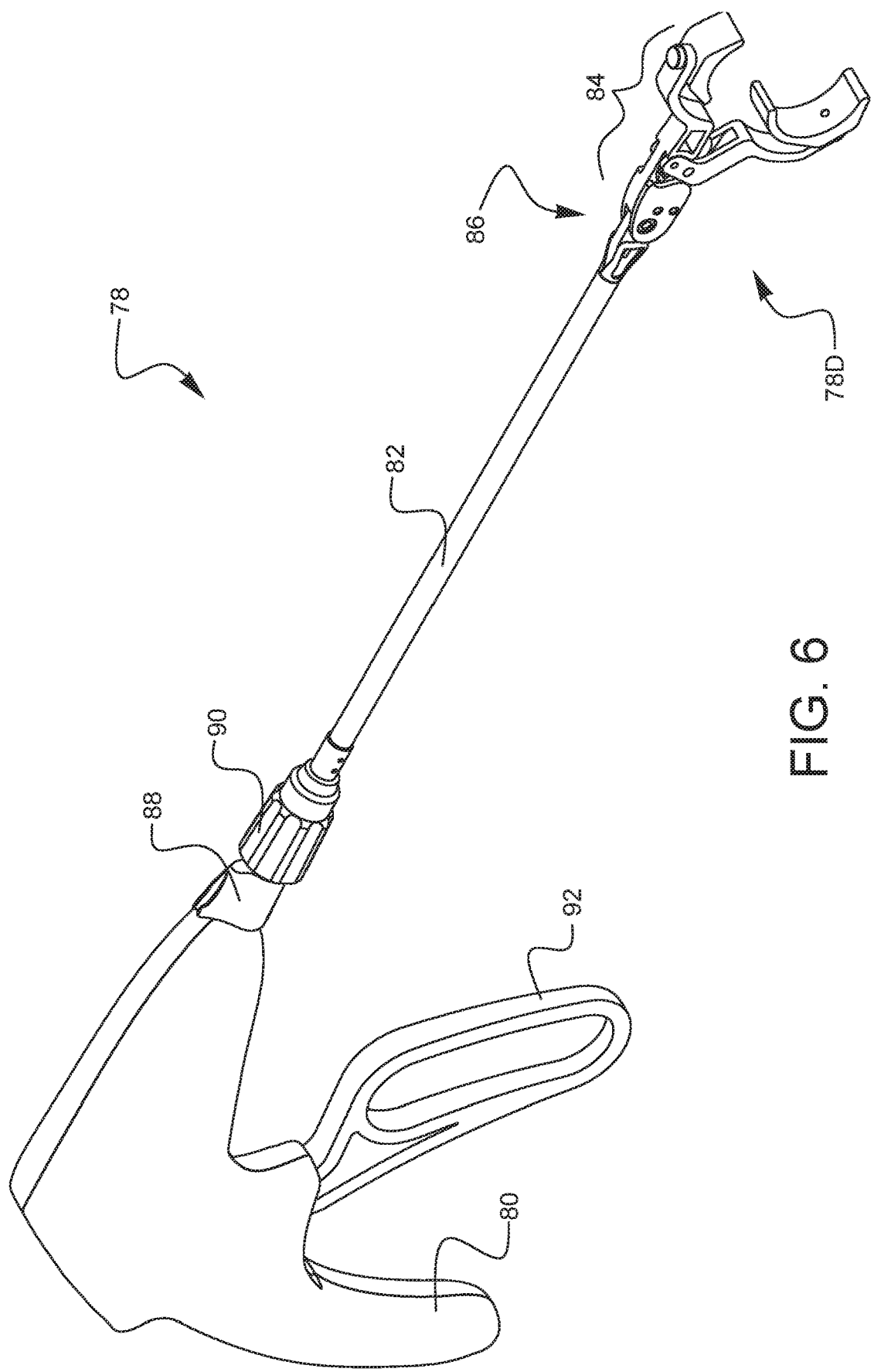
FIG. 6 is a perspective view of one embodiment of an insertion tool for grasping a VAD pump.

An insertion tool 78 may be provided for grasping the HMIII pump by its inflow tube. FIG. 6 is a perspective view of one embodiment of an insertion tool 78 for just such use. The insertion tool 78 has a handle 80 from which a shaft 82 extends. At the distal end 78D of the device 78, a set of gimballing clamp jaws 84 is coupled to the shaft 82 by an articulation joint 86. The shaft 82 may be rotated by turning a rotation knob 88, and the gimballing clamp jaws 84 may be articulated by rotating an articulation knob 90. The insertion tool 78 also has a lever 92 which is pivotable relative to the handle 80. When the lever 92 is in the position illustrated in FIG. 6, the gimbaled clamp jaws 84 are open as also illustrated. When the lever 92 is squeezed towards the handle 80, the gimballed clamp jaws 84 close.

Figure 7:
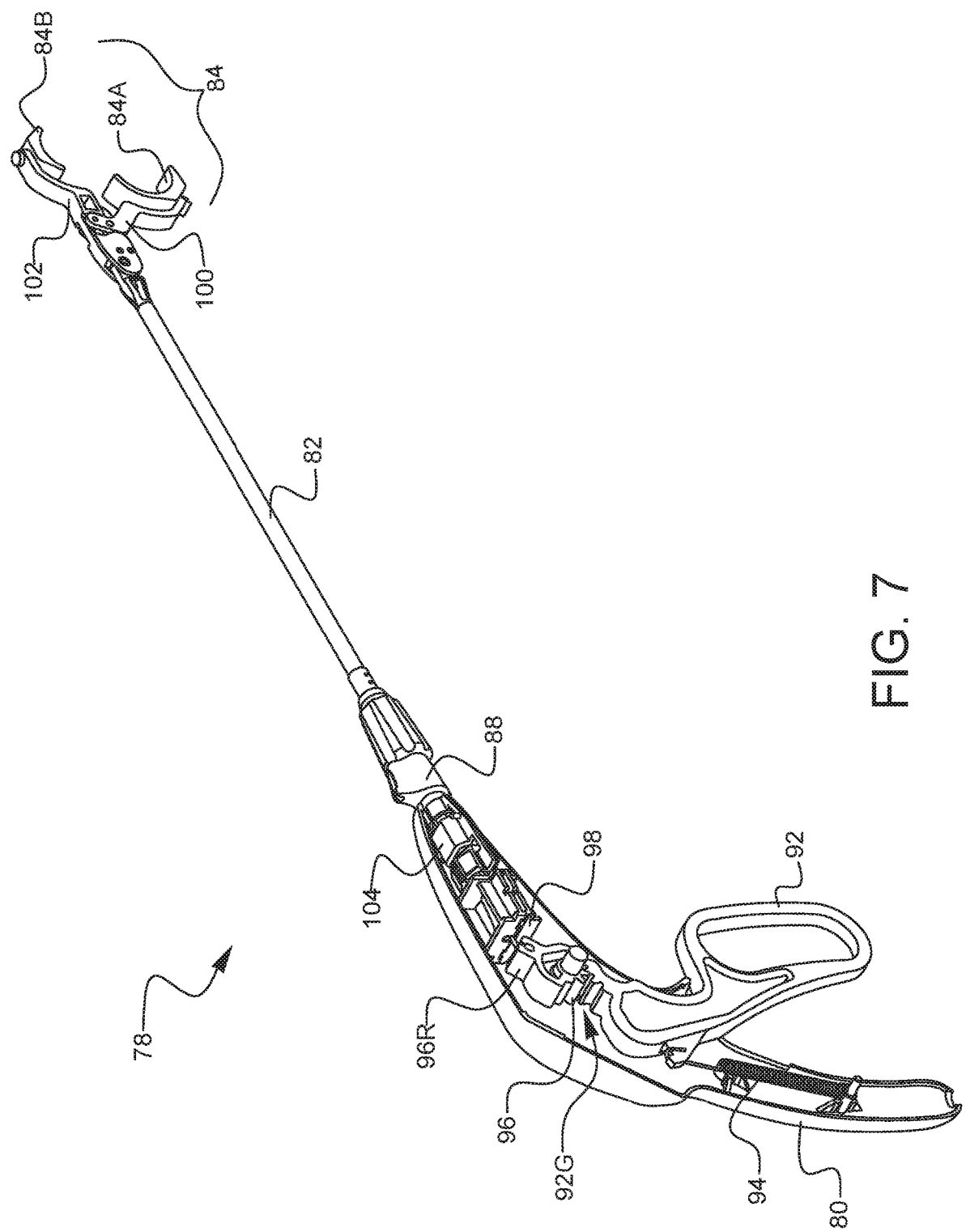
FIG. 7 is a partially exposed perspective view of the insertion tool of FIG. 6, with a portion of the handle removed to show the inner workings.

FIG. 7 is a partially exposed perspective view of the insertion tool 78 of FIG. 6, with a portion of the handle 80 removed to show the inner workings. The lever 92 is kept in its normal position (corresponding to the gimballed clamp jaws 84 being open) by a biasing element or spring 94. The lever 92 has a lever gear 92G which engaged a drive gear 96. The drive gear 96 has a receiver 96R which is coupled to a drive wire 98 which extends down the shaft 82 where it is also coupled to the opening clamp arm 100. When the lever 92 is squeezed, the lever gear 92G rotates, causing the drive gear 96 also to rotate, by which the drive gear receiver 96R pulls the drive wire 98, which therefore causes the movable clamp arm 100 to pivot towards the fixed clamp arm 102. This brings the first and second clamp jaws 84A and 84B together. The rotation knob 88 is coupled to the shaft 82 and also extends into the handle 80 where it is rotatably supported by a rotation adapter 104.

FIGS. 8A-8E are exploded perspective views of portions of the insertion tool 78 of FIGS. 6 and 7 which illustrate their assembly. Referencing FIG. 8A, the rotation knob 88 is shown attached to the shaft 82. The faceted portion 88F of the rotation knob 88 which is rotatably supported by the rotation adapter 104 is visible. An articulation wire 106 is placed into the shaft 82, and a slideable drive gear 108 is placed into a slot 110 in shaft 82 where it is coupled to a proximal end 106P of the articulation wire 106. The articulation knob 90 is slid over the shaft 82, is threaded onto the threads 108T of the slideable drive gear 108, and then also held constrained by a snap interference with one or more grooves 112 on the shaft 82. This ensures the articulation knob 90 can rotate around the shaft 82 but can't slide up and down the shaft 82. The result is that rotating the articulation knob 90 in one direction will cause the slideable drive gear 108 to pull the articulation wire 106 into the shaft 82, while rotating the articulation knob 90 in an opposite direction will cause the slideable drive gear to push the articulation wire 106 out of the shaft 82.

Figure 8A:
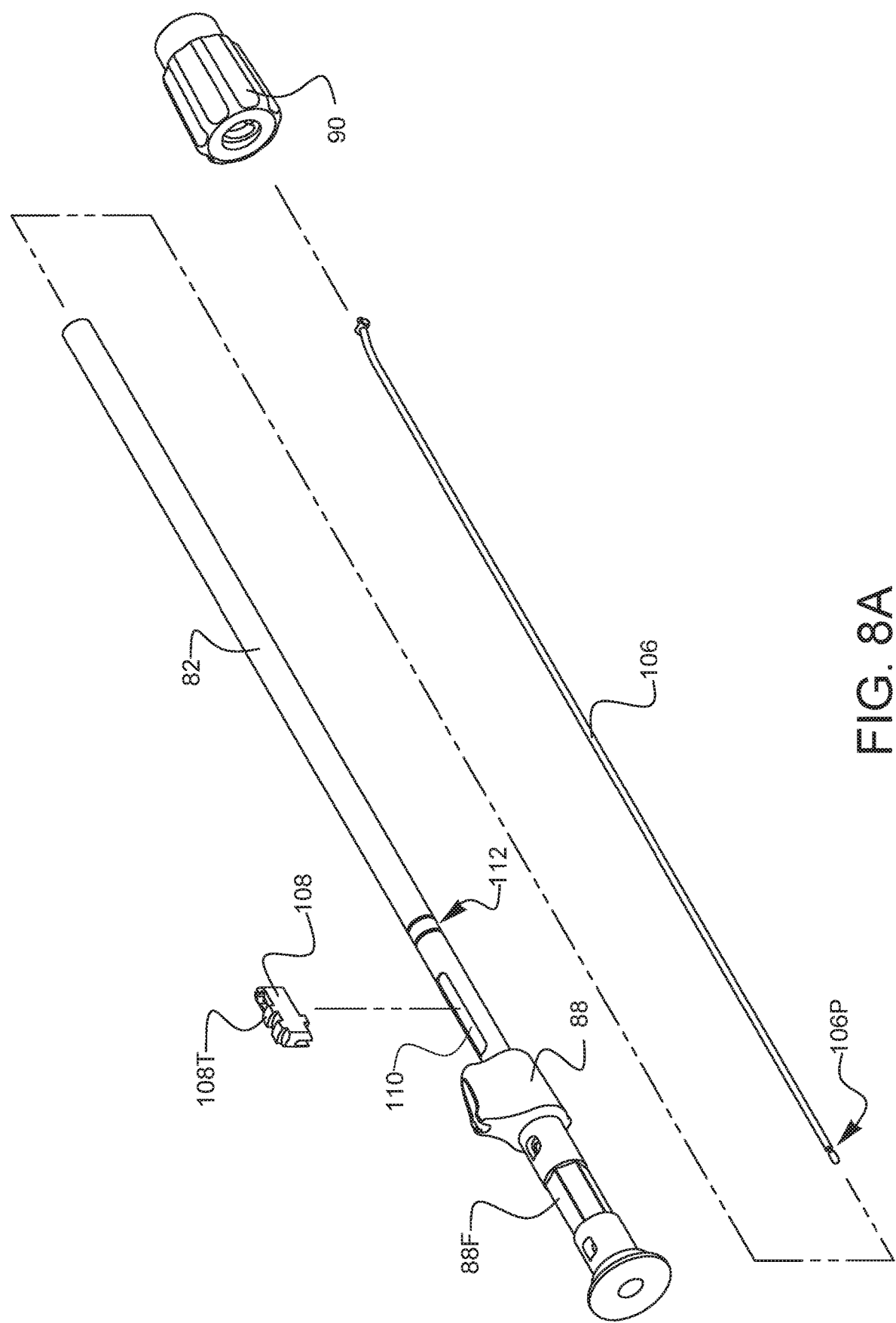
Figure 8B:
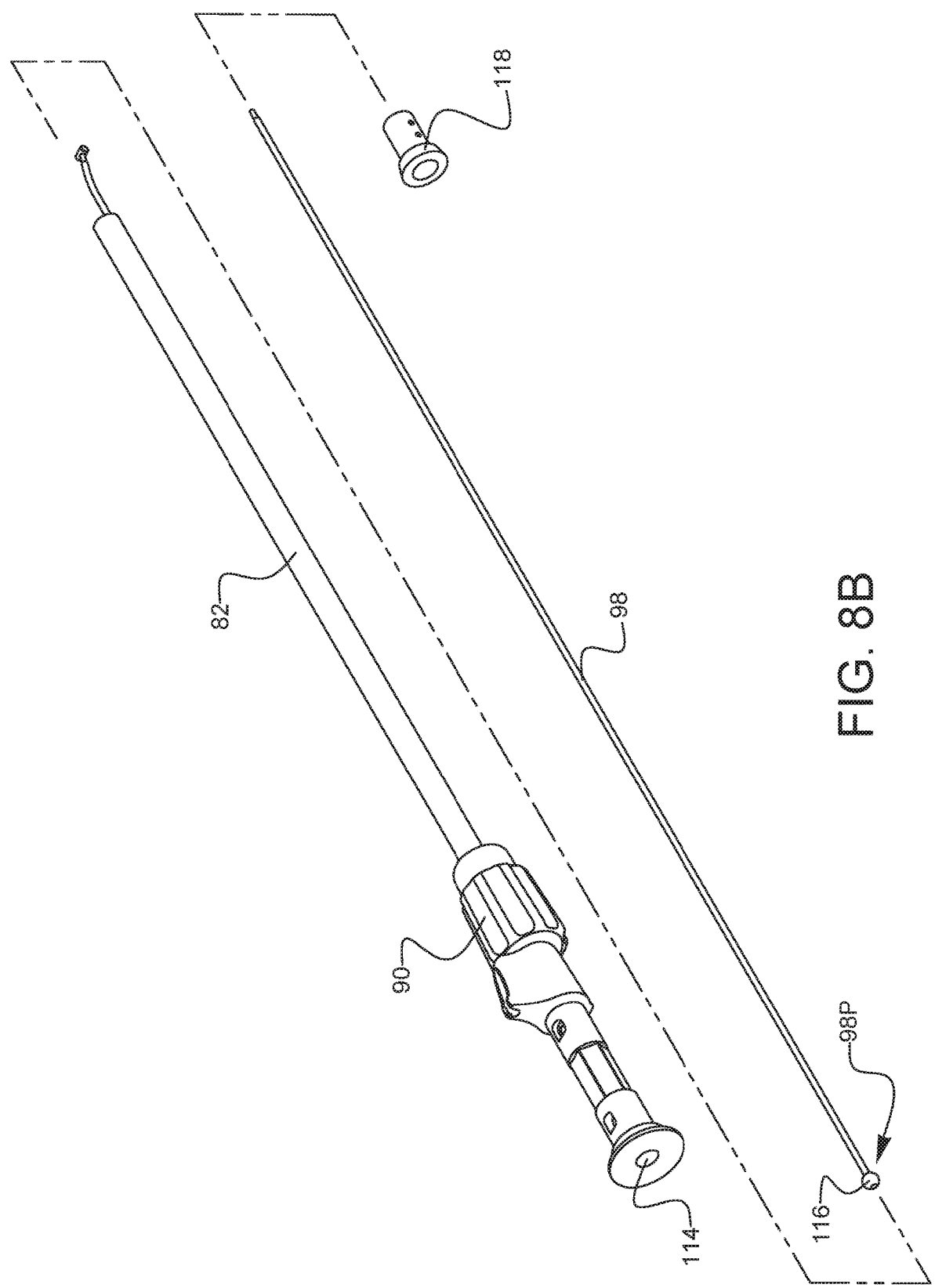

As shown in FIG. 8B, a proximal end 98P of the drive wire 98 is placed into the shaft 82 where it exits an opening 114 in the assembly from FIG. 8A. In this embodiment, the proximal end 98P of the drive wire 98 has a ball connector 116 which engages the drive gear receiver 96R discussed previously. A collar 118 may also be placed over the shaft 82 and attached in place to help prevent the articulating knob 90 from sliding up and down the shaft 82. In such embodiments, the grooves 112 discussed previously would not be needed because the collar 118 can handle the necessary restraining.

Figure 8C:
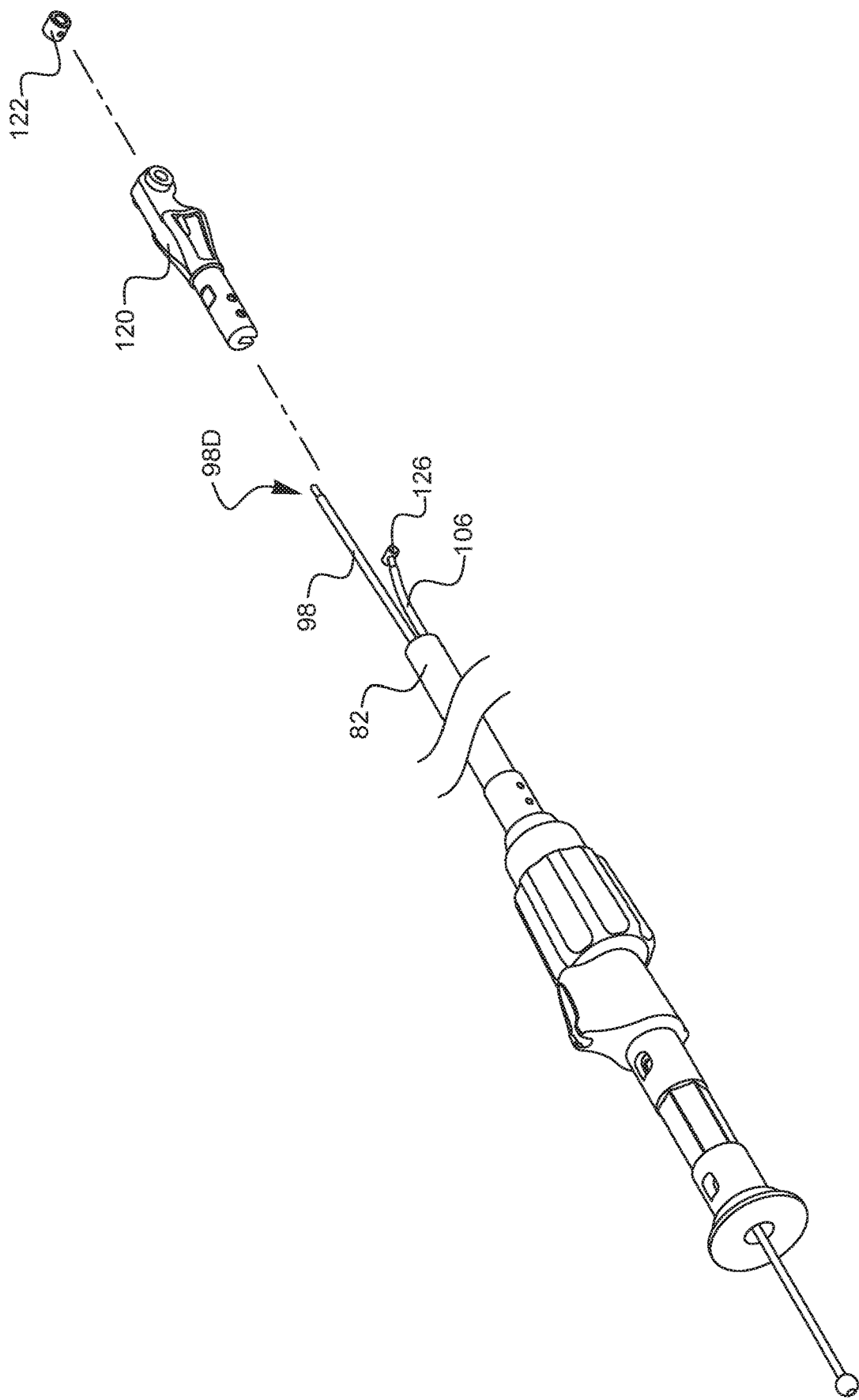

As shown in FIG. 8C, an articulation joint 120 is placed over the drive wire 98 and the articulation wire 106 and into the shaft 82. A barrel connector 122 is coupled to the distal end 98D of the drive wire 98.

As shown in FIG. 8D, the fixed clamp arm 102 is attached around the articulation joint 120 such that it is pivotable around pivot point 124 also being connected to the barrel connector 126 on the end of the articulation wire 106. The term "fixed" as applied to the fixed clamp arm 102 does not mean that the clamp arm 102 does not move at all. In fact, the fixed clamp arm 102 is able to pivot around the articulation joint 120 at an angle determined by the position of the articulation wire 106 as driven by the articulation knob 90. The "fixed" aspect of the fixed clamp arm 102 is that it does not move relative to the movable clamp arm 100 when the lever 92 is squeezed. Instead, it is the movable clamp arm 100 which is movable towards the fixed clamp arm 102 in this embodiment. A cam plate 128 is also coupled to the opposite side of the articulation joint 120 to add additional support for the barrel connector 126. Additionally, one of the gimballing clamp jaws 84B is pivotably coupled to the fixed clamp arm 102 at point 130 with a post 132.

Figure 8E:
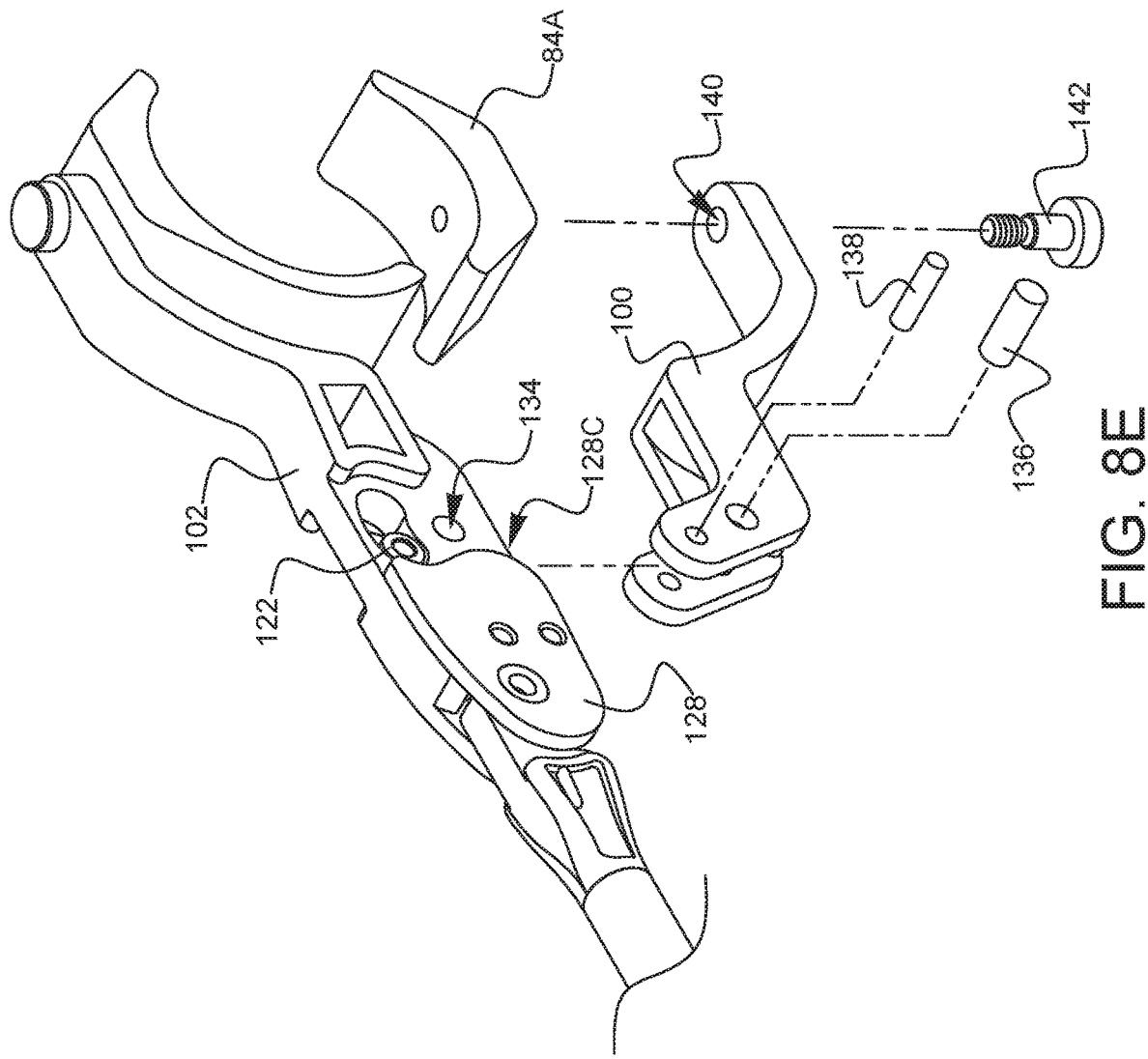

As shown in FIG. 8E, the movable clamp arm 100 is pivotably coupled to the fixed clamp arm 102 at pivot point 134 by a pin 136. The movable clamp arm 100 is also coupled to the barrel connector 122 by another pin 138. When the drive wire moves the barrel connector 122 distally, the movable clamp arm 100 is rotated about the cam surface 128C of cam plate 128 into the open position illustrated in FIG. 7 where clamp jaws 84A and 84B are apart. When the drive wire moves the barrel connector 122 proximally, the movable clamp arm 100 is rotated into a closed position where the clamp jaws 84A and 84B come towards each other and therefore may hold onto a portion of a VAD. Additionally, one of the gimballing clamp jaws 84A is pivotably coupled to the movable clamp arm 100 at point 140 with a post 142.

Figure 9:
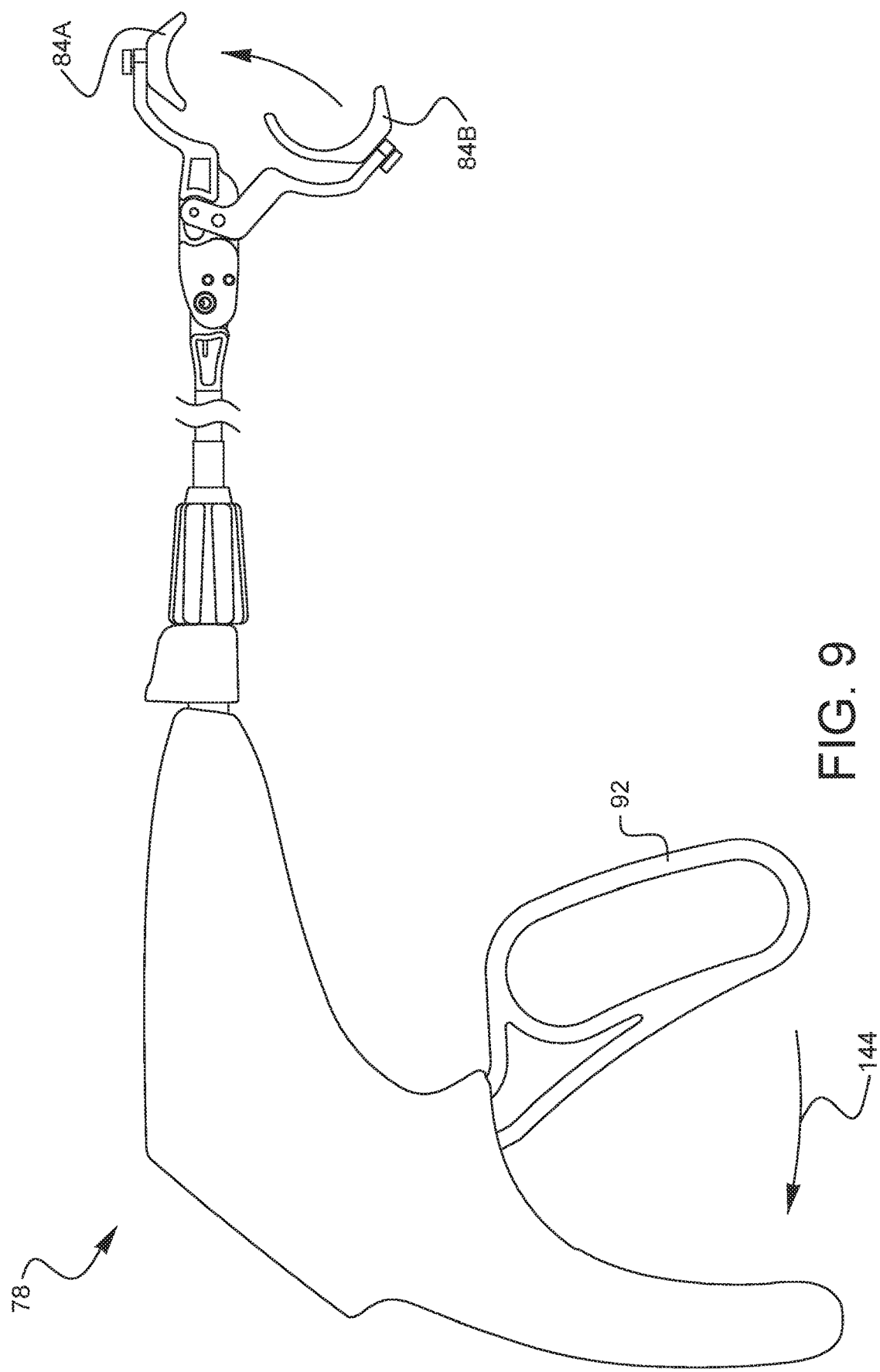
FIG. 9 is a side view of the insertion tool of FIG. 6 illustrating the closing of the clamp jaws when the device lever is squeezed.

FIG. 9 is a side view of the insertion tool 78 of FIG. 6 illustrating the closing of the clamp jaws 84A, 84B when the device lever 92 is squeezed 144.

Figure 10:
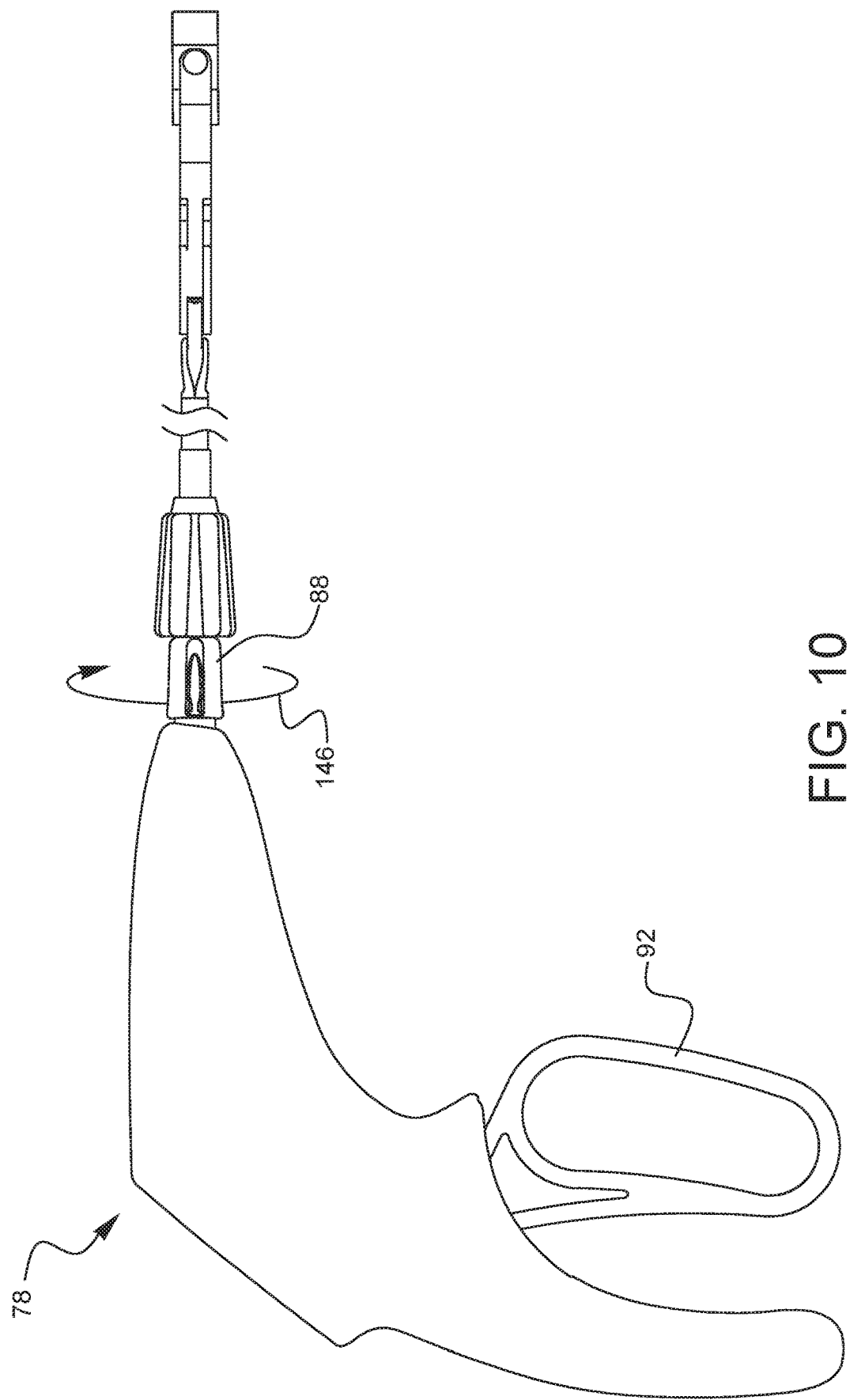
FIG. 10. is a side view of the insertion tool of FIG. 6 illustrating rotation of the shaft when the rotation fin is rotated.

FIG. 10. is a side view of the insertion tool 78 of FIG. 6 illustrating rotation of the shaft 82 when the rotation knob 88 is rotated 146. It should be noted that lever 92 is shown still squeezed in this view, but the lever 92 does not have to be squeezed in order for the rotation knob 88 to be rotated.

Figure 11:
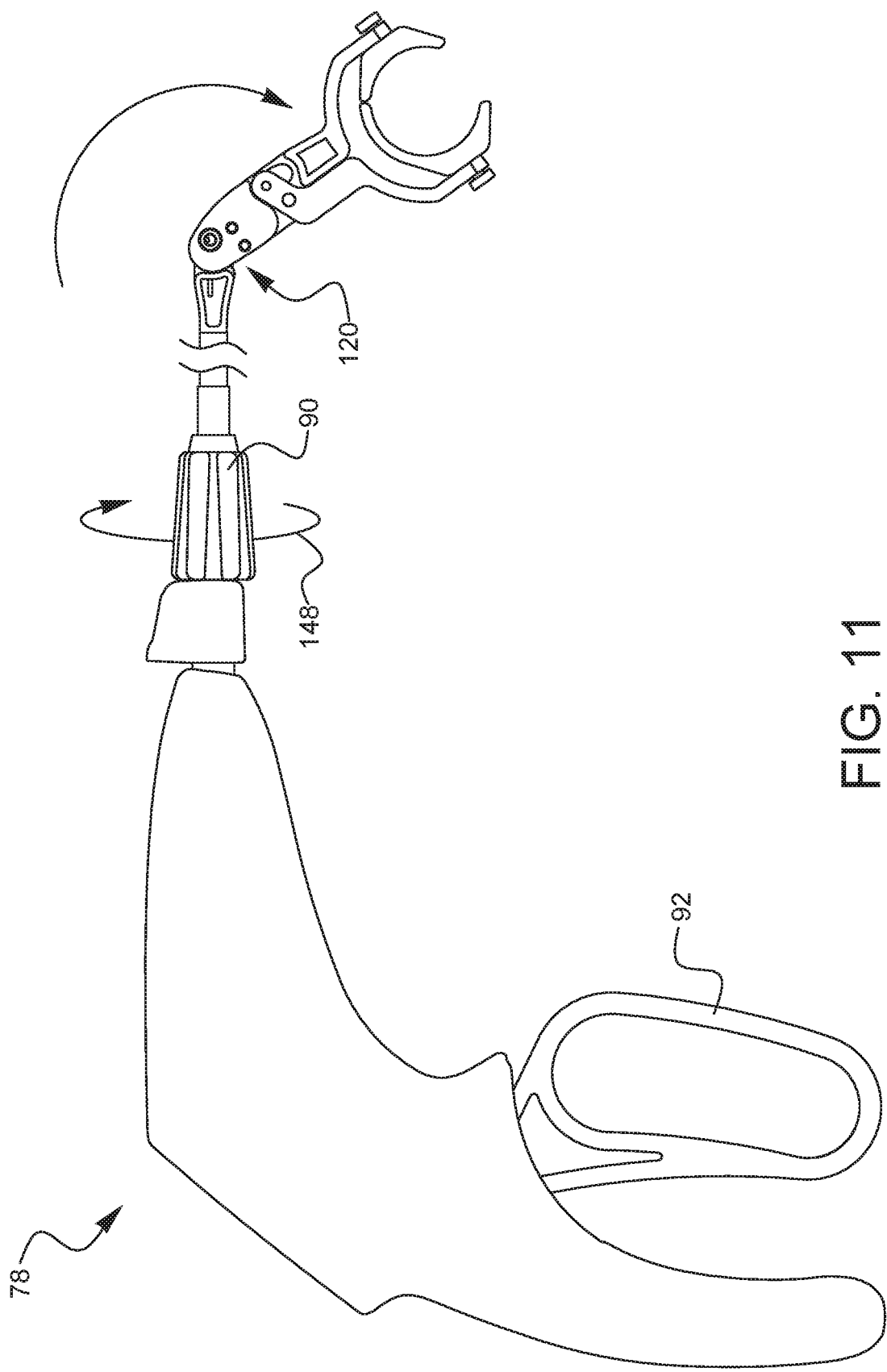
FIG. 11 is a side view of the insertion tool of FIG. 6 illustrating articulation of the articulation joint when the articulation knob is rotated.
Figure 12A:
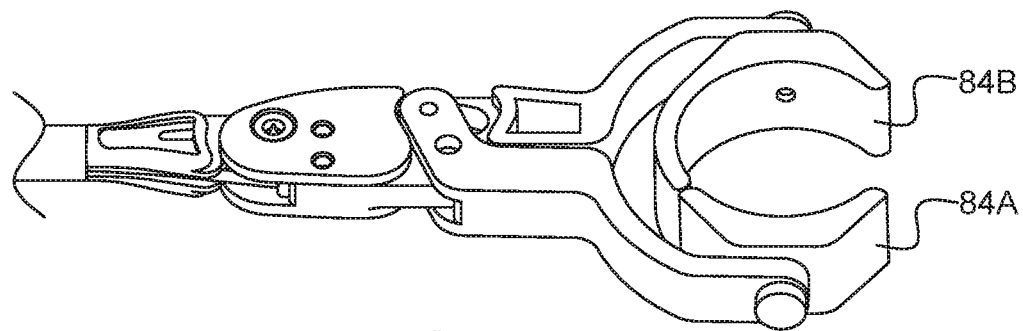
FIGS. 12A-12D illustrate example positions of the gimbaled clamp jaws. The gimbaled clamp jaws are free to pivot on their pivot points.
Figure 12B:
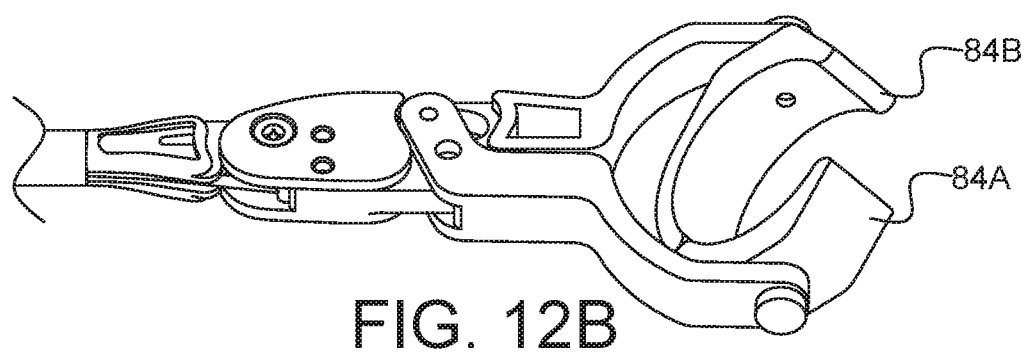
Figure 12C:
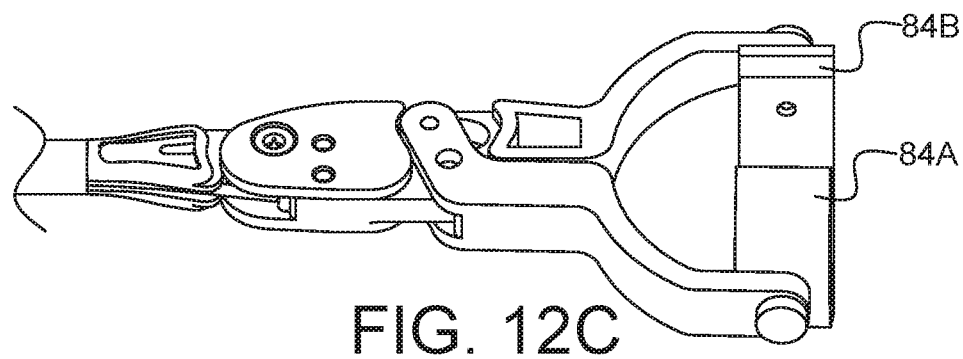
Figure 12D:
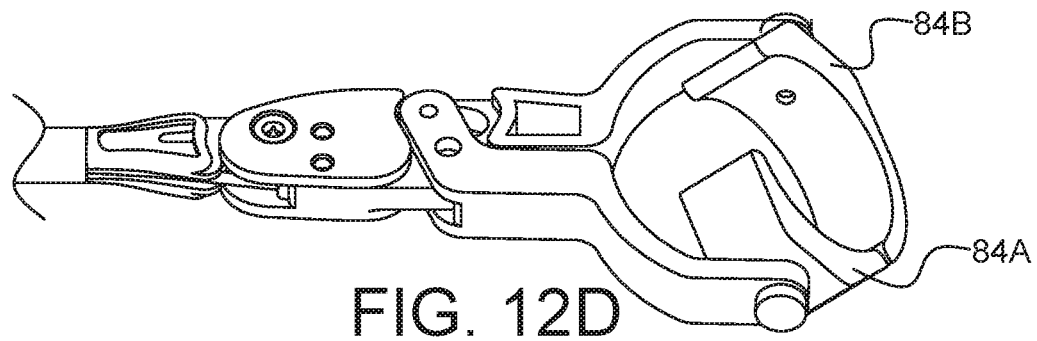

FIG. 11 is a side view of the insertion tool 78 of FIG. 6 illustrating articulation at the articulation joint 120 when the articulation knob 90 is rotated 148. It should be noted that lever 92 is shown still squeezed in this view, but the lever 92 does not have to be squeezed in order for the articulation knob 90 to be rotated.

FIGS. 12A-12D illustrate example positions of the gimbaled clamp jaws 84A, 84B. For the sake of visualization in these views, the clamp jaws 84A, 84B are in the closed or clamped position around a non-visible tube of a VAD. This explains why the clamp jaws 84A, 84B which are free to gimbal independently of each other are tracking with each other in the different views of FIGS. 12A-12D. This gimballing action while the clamp jaws 84A, 84B are closed provides helpful mobility as a surgeon is using the insertion tool to place a VAD into a patient through a mini thoracotomy.

Figure 13:
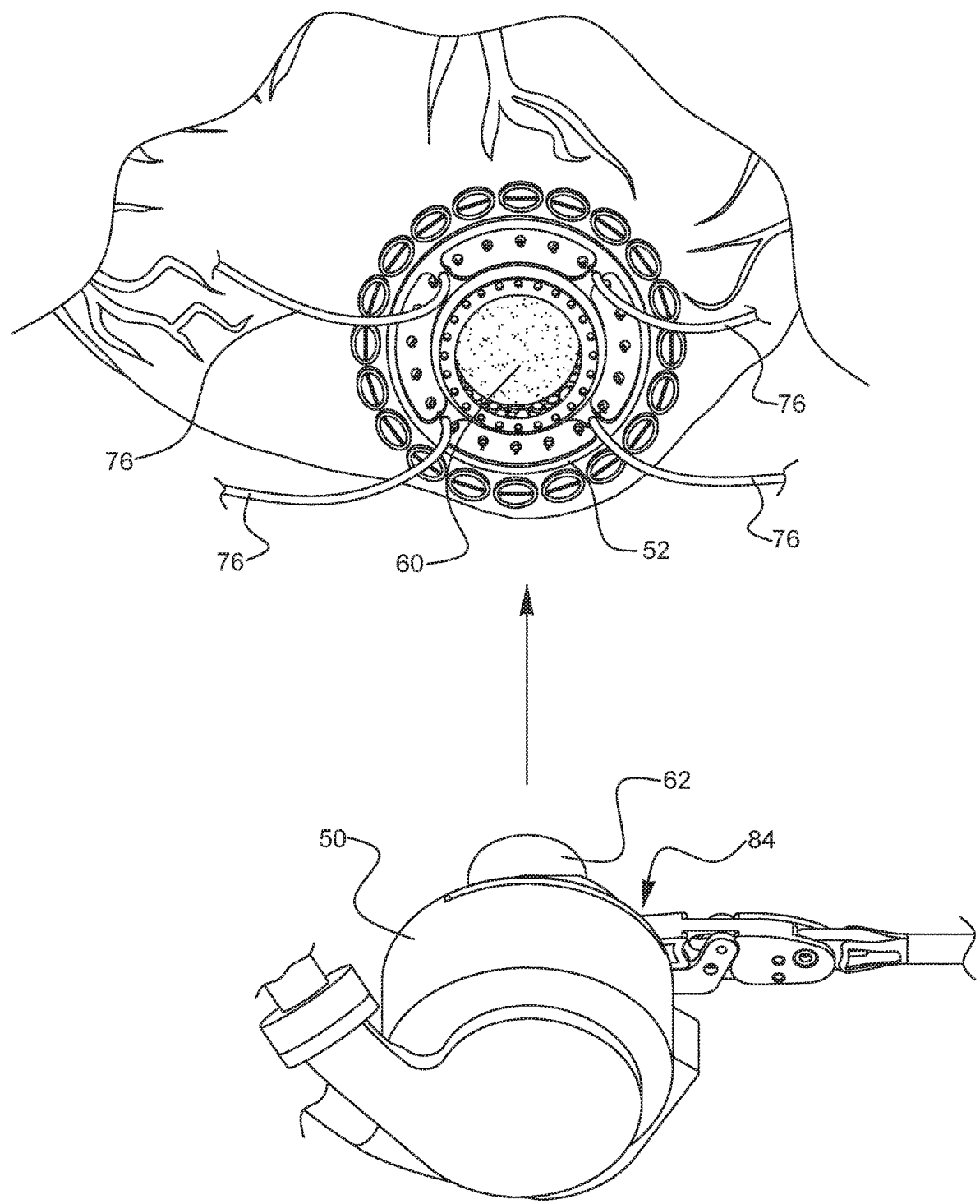
FIG. 13 shows a representation of the gimbaled clamp jaws holding the inflow tube of an HMIII LVAD.

The insertion tool provides articulation, clamping, and a gimbaled set of clamp jaws to provide mobility when inserting the pump through a small thoracotomy which the human hand would be too large to provide in minimally invasive surgery. FIG. 13 shows a representation of the gimbaled clamp jaws 84 holding the inflow tube 62 of an HMIII LVAD 50. The jaws 84 are sized so that a portion of the pump inflow 62 still protrudes from them when the insertion tool is holding the pump 50. In this way, the inflow tube 62 may still be worked into the opening 60 in the flange 52 where the pump 50 should be inserted. Once the inflow tube 62 is aligned with the flange opening 60, the insertion tool may release the pump 50 and be removed from the patient. The pump 50 is pushed fully against the flange 52 and attached in the usual fashion (known to those skilled in the art) from this point.

Figure 14:
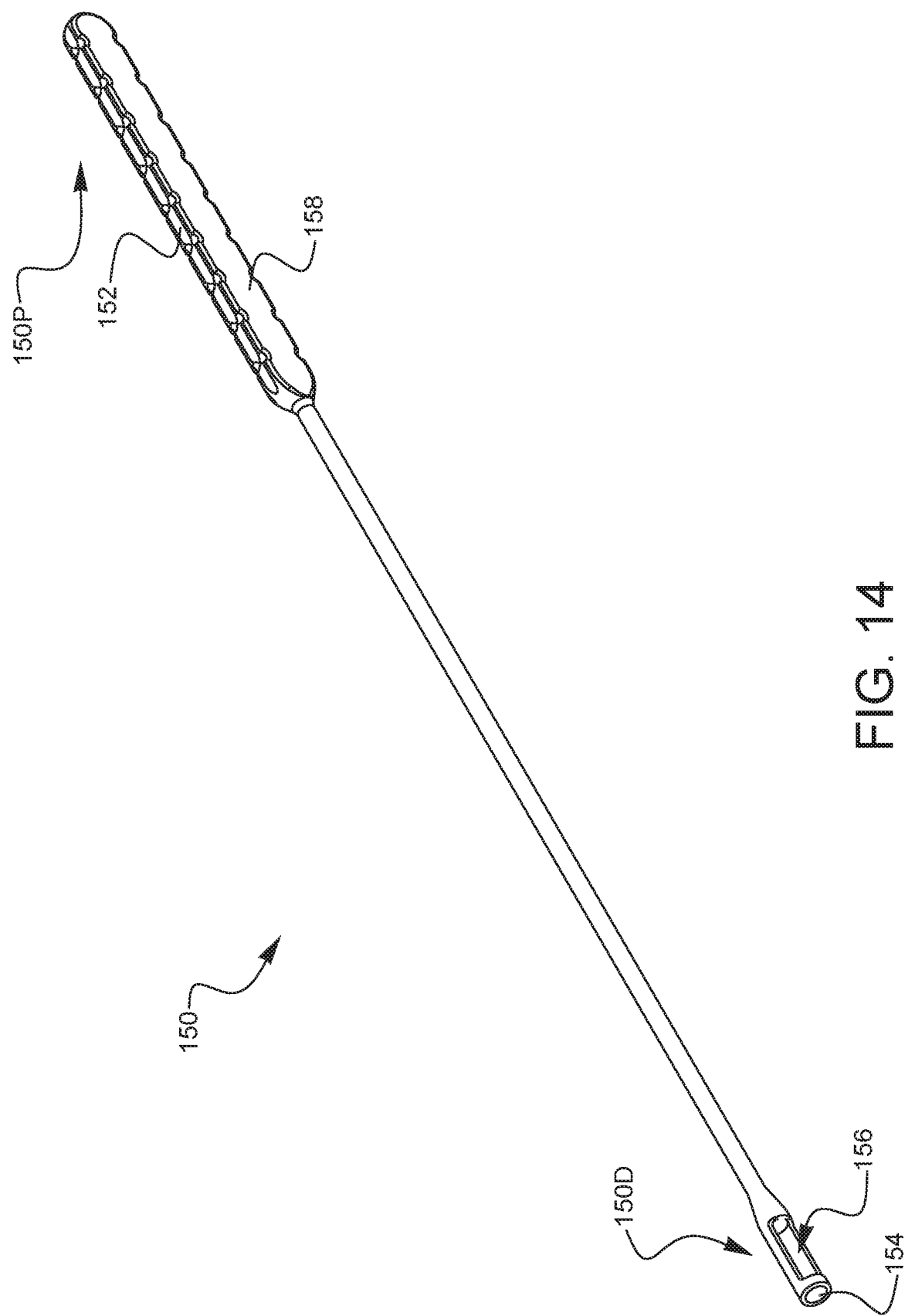
FIG. 14 is a perspective view of one embodiment of a pushing tool.

During the installation of the pump, if it becomes necessary to push down on the flange, a pushing tool 150 is also provided. FIG. 14 is a perspective view of one embodiment of a pushing tool 150. FIGS. 15A, 15B, and 15C are top, bottom, and side elevational views, respectively of the pushing tool from FIG. 14. The pushing tool 150 has a proximal end 150P and a distal end 150D. The proximal end 150P has a textured grip 152 to assist with holding the pushing tool 150. The pushing tool 150 is designed to have a distal opening 154 in communication with a side opening 156. In this embodiment, the proximal end 150P also has an orientation feature 158, which can assist a user of the pushing tool 150 with maintaining awareness of where the side opening 156 is pointing. This is especially useful when the side opening 156 of the pushing tool 150 is inside a patient and can't be directly visualized.

The distal opening 154 and the side opening 156 are sized to fit over the MINI-RUMEL™ tubes 76 installed and described earlier. This allows the pushing tool 150 to ride down the tube 76 and contact the crossbar 64 of the frame 52, since the tube 76 has been cinched against the frame's crossbar 64. FIG. 16 illustrates an example where the pushing tool 150 has been placed over such a tube 76. With this feature, a surgeon can use the pushing tool 150 to manipulate the frame 52 in a mainly blind situation when working through a mini thoracotomy while still having confidence that she will not be pushing on the heart itself. The Rumel tube 76 acts as a guide for the pushing tool 150 to ensure it aligns with the crossbar 64.

Various advantages of a minimally invasive LVAD installation system and method have been discussed above. Embodiments discussed herein have been described by way of example in this specification. It will be apparent to those skilled in the art that the forgoing detailed disclosure is intended to be presented by way of example only and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A surgical instrument comprising:
   a handle;
   a lever pivotably coupled to the handle, the lever being displaceable relative to the handle between a first position and a second position;
   a shaft extending from a proximal end to a distal end, wherein the proximal end of the shaft is coupled to the handle; and
   a clamp jaw assembly comprising:
   a base member coupled to the distal end of the shaft;
   a first arm coupled to the base member;

a first jaw member rotatably coupled to a portion of the first arm, the first jaw member being rotatable relative to the first arm about a first axis extending through the portion of the first arm, wherein the first jaw member includes a gripping surface having the shape of a segment of a cylinder;

a second arm pivotably coupled to the base member, the second arm being operatively coupled to the lever such that when the lever is in the first position, the second arm is in a first position relative to the first arm and when the lever is in the second position, the second arm is in a second position relative to the first arm; and a second jaw member rotatably coupled to a portion of the second arm, the second jaw member being rotatable relative to the second arm about a second axis extending through the portion of the second arm, wherein the second jaw member includes a gripping surface having the shape of a segment of a cylinder.

2. The surgical instrument of claim 1, wherein the first axis of the first jaw member is not parallel to a longitudinal axis of the shaft.

3. The surgical instrument of claim 1, further comprising: an articulating joint disposed at or adjacent to the distal end of the shaft, wherein a distal end of the articulating joint is pivotably coupled to a proximal portion of the base member of the clamp jaw assembly such that the base member is pivotable relative to the shaft.

4. The surgical instrument of claim 3, further comprising: an articulation knob rotatably coupled to the proximal end of the shaft; and an articulation wire having a distal end and a proximal end, wherein at least a portion of the articulation wire extends within the shaft, and wherein the proximal end is operatively coupled to the articulation knob and wherein the distal end is coupled to a portion of the base member of the clamp jaw assembly such that a displacement of the articulation wire by a rotation of the articulation knob pivots the base member of the clamp jaw assembly about the distal end of the articulating joint.

5. The surgical instrument of claim 1, wherein the first arm of the clamp jaw assembly is fixedly coupled to the base member.

6. The surgical instrument of claim 1, wherein the first arm of the clamp jaw assembly is integrally formed with the base member.

7. The surgical instrument of claim 1, wherein the proximal end of the shaft is rotatably coupled to the handle such that the shaft is rotatable about a longitudinal axis of the shaft.

8. The surgical instrument of claim 1, further comprising:
a drive wire having a distal end and a proximal end, wherein at least a portion of the drive wire extends within the shaft, wherein the proximal end is coupled to a portion of the lever, and wherein the distal end is coupled to a portion of the clamp jaw assembly such that the second arm is operatively coupled to the lever by the drive wire.

9. The surgical instrument of claim 8, wherein the distal end of the drive wire is coupled to a portion of the second arm such that the second arm is operatively coupled to the lever by the drive wire.

10. An assembly configured to be coupled to a distal end of a shaft of a surgical instrument, the assembly comprising:
a clamp jaw assembly comprising:
a base member configured to be coupled to the distal end of the shaft;
a first arm coupled to the base member;
a first jaw member rotatably coupled to a portion of the first arm, the first jaw member being rotatable relative to the first arm about a first axis extending through the portion of the first arm, wherein the first jaw member includes a gripping surface having the shape of a segment of a cylinder;
a second arm pivotably coupled to the base member, the second arm configured to be operatively coupled to an actuation mechanism of the surgical instrument such that when the actuation mechanism is in a first position, the second arm is in a first position relative to the first arm and when the actuation mechanism is in a second position, the second arm is in a second position relative to the first arm; and
a second jaw member rotatably coupled to a portion of the second arm, the second jaw member being rotatable relative to the second arm about a second axis extending through the portion of the second arm, wherein the second jaw member includes a gripping surface having the shape of a segment of a cylinder.

11. The assembly of claim 10, further comprising an articulating joint configured to be disposed at the distal end of the shaft, wherein a distal end of the articulating joint is pivotably coupled to a proximal portion of the base member of the clamp jaw assembly such that the base member is pivotable relative to the articulating joint.

12. The assembly of claim 10, wherein the first arm of the clamp jaw assembly is fixedly coupled to the base member.

13. The assembly of claim 10, wherein the first axis of the first jaw member is not parallel to a longitudinal axis of the shaft.

* * * * *